United States Patent

Kobayashi et al.

Patent Number: 5,354,574
Date of Patent: Oct. 11, 1994

[54] METHOD FOR PRODUCING OPTICAL FIBER HAVING FORMYL GROUPS ON CORE SURFACE THEREOF

[75] Inventors: Takeshi Kobayashi; Shinji Iijima, both of Nagoya; Ken-ichi Shimada, Gifu; Kazue Ohe, Gifu; Yasunori Sakai, Gifu, all of Japan

[73] Assignee: Ibiden Co., Ltd., Gifu, Japan

[21] Appl. No.: 80,615

[22] Filed: Jun. 22, 1993

[30] Foreign Application Priority Data

Jun. 23, 1992 [JP] Japan ............................ 4-189983
Aug. 28, 1992 [JP] Japan ............................ 4-254171
Jan. 19, 1993 [JP] Japan ............................ 5-024853
Jan. 19, 1993 [JP] Japan ............................ 5-024854

[51] Int. Cl.$^5$ ............................................. B05D 5/06
[52] U.S. Cl. ......................... 427/21.3; 427/337; 427/377; 427/163.2; 427/430.1; 427/384
[58] Field of Search ............... 427/163, 337, 430.1, 427/377, 2, 384

[56] References Cited

U.S. PATENT DOCUMENTS

| | | | |
|---|---|---|---|
| 3,999,834 | 12/1976 | Ohtonio et al. | 427/163 |
| 4,166,105 | 8/1979 | Hirschfeld . | |
| 4,558,014 | 12/1985 | Hirschfeld et al. | 436/527 |
| 4,582,809 | 4/1986 | Block et al. . | |
| 4,666,862 | 5/1987 | Chan | 436/501 |
| 4,708,882 | 11/1987 | Asano et al. | 427/145 |
| 4,716,121 | 12/1987 | Block et al. | 436/514 |
| 4,818,710 | 4/1989 | Sutherland et al. | 436/527 |
| 4,925,268 | 5/1990 | Iyer et al. | 350/96.29 |
| 5,015,843 | 5/1991 | Seitz et al. | 5/227.21 |
| 5,019,350 | 5/1991 | Rhum et al. | 422/82.07 |
| 5,117,480 | 5/1992 | Yamamoto et al. | 385/145 |

FOREIGN PATENT DOCUMENTS

| | | |
|---|---|---|
| 58-30667 | 2/1983 | Japan . |
| 58-61468 | 4/1983 | Japan . |
| 59-81560 | 5/1984 | Japan . |
| 60-24450 | 2/1985 | Japan . |
| 60-36963 | 2/1985 | Japan . |
| 60-252265 | 12/1985 | Japan . |
| 61-88155 | 5/1986 | Japan . |
| 61-191965 | 8/1986 | Japan . |
| 61-292044 | 12/1986 | Japan . |
| 62-66143 | 3/1987 | Japan . |
| 62-79333 | 4/1987 | Japan . |
| 62-79334 | 4/1987 | Japan . |
| 62-501102 | 4/1987 | Japan . |
| 62-123358 | 6/1987 | Japan . |
| 63-289001 | 11/1988 | Japan . |
| 64-47952 | 2/1989 | Japan . |
| WO9013029 | 1/1990 | PCT Int'l Appl. . |
| WO9313418 | 8/1993 | PCT Int'l Appl. . |

OTHER PUBLICATIONS

Okubo et al., "Improvement . . . Modification", AICHE Journal, Jun. 1988, vol. 34, No. 6, pp. 1031–1033.
Koenig et al., "Raman . . . Surfaces", Materials Science and Engineering, 20 (1975) 127–135 (no month).
Shioji et al., "Adsorption . . . Glass", Wakayama Technical Higher Specialized School Research Memoir, No. 22 (1987), pp. 54–57 (no month).
Yazawa et al., "Analysis . . . Glass", Yogyo-Kyokai--

(List continued on next page.)

Primary Examiner—Janyce Bell
Attorney, Agent, or Firm—Birch, Stewart, Kolasch & Birch

[57] ABSTRACT

The present invention is directed to a method for producing an optical fiber having formyl groups on a core surface. In one embodiment, a plastic optical fiber having formyl groups on a core surface is obtained by immersing the core surface of the plastic optical fiber in a treating solution containing at least a 0.5 to 40 mM alkali metal hydroxide and a compound having formyl groups in water or lower alcohol solvent. In the other embodiment, a plastic optical fiber having formyl groups on a core surface is obtained by introducing a vic-diol group, a primary hydroxyl group or an alkenyl group on the core surface, and then oxidizing it. Turbidity on the core surface of the optical fiber thus obtained is minimized, thereby reducing the transmittance losses of light.

16 Claims, 3 Drawing Sheets

OTHER PUBLICATIONS

Shi Journal of Ceramic Association, 95 (12) 1987, pp. 42–47 (no month).

Perry et al., "Structural . . . Phases", J. Chem. Soc. Faraday Trans., 1991, 87 (24), 3857–3862 (no month).

Perry et al., "Structural . . . Phases", J. Chem. Soc. Faraday Trans, 1991, 87 (5), 761–766 (no month).

H. A. Weetall (editor), "Imobilized . . . Peptides", Enzymology, 1975 (no month).

Marciniec et al., "Silane . . . 3-Aminopropyltriethoxysilane", International Polymer Science and Technology, vol. 18, No. 8, 1991, pp. T/62–T/67 (no month).

Chang et al., "The Structure . . . Surfaces", Journal of Colloid and Interface Science, vol. 74, No. 2, Apr. 1980, pp. 396–404.

Yazawa et al., "Reactivity . . . Compounds", Journal of Nippon Ceramics Association Treatise, 96(6), pp. 630–633 (1988) (Abstract) (no month).

Okuda et al., "Reaction . . . Compounds", Journal of Fermentation and Bioengineering, vol. 71, No. 2, pp. 100–105 (1991) (no month).

Vo-Dinh et al., Anal. Chem., vol. 59, pp. 1226–1230 (1987) (no month).

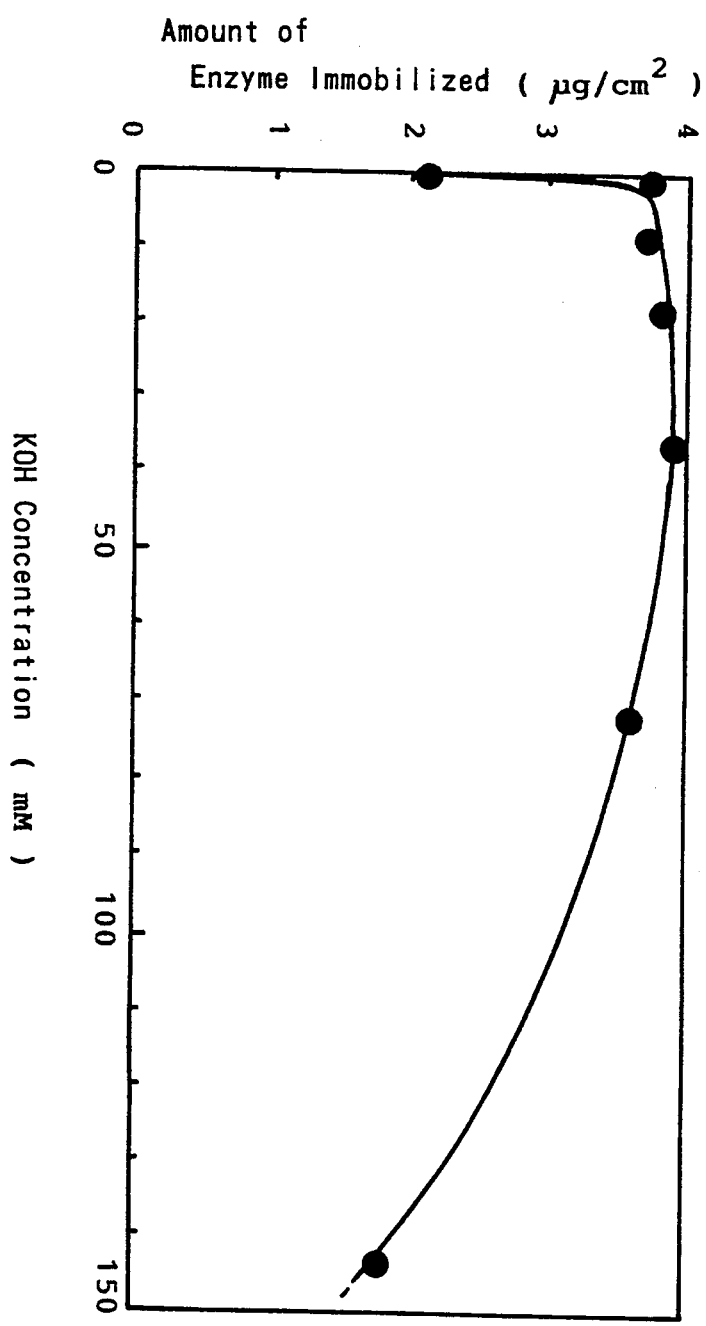
F I G. 1

METHOD FOR PRODUCING OPTICAL FIBER HAVING FORMYL GROUPS ON CORE SURFACE THEREOF

FIELD OF THE INVENTION

The present invention relates to a method for producing an optical fiber having formyl groups on a core surface thereof, more specifically to a method for producing an optical fiber for immobilization of an immunological substance which can be used in an immunoassay for biomaterials.

BACKGROUND OF THE INVENTION

Traditionally, as a method for immunoassay of biomaterials, fluoroimmunoassay has been conducted using an optical fiber with an immunological substance such as an antigen or antibody immobilized thereto.

In this case, to facilitate the immobilization of an immunological substance on the surface of the optical fiber, a crosslinking agent highly reactive with the amino group in the antigen or antibody is introduced on the surface of the optical fiber. For example, WO90/13029 proposes a method wherein an optical fiber is reacted with a dialdehyde such as glutaraldehyde or succinaldehyde to introduce formyl groups on a core surface thereof, thereby facilitating immobilization of an immunological substance on the surface of the optical fiber, and the formyl groups are reacted and bound with the amino group in a bioactive component such as an antigen or antibody to immobilize the immunological substance to the optical fiber.

Specifically, in the method of WO90/13029, a plastic optical fiber mainly composed of a resin having an ester structure is used as an immobilization carrier for immunological substances such as bioactive components, and formyl groups are introduced on a core surface of the plastic optical fiber by carrying out the reaction while immersing the core surface of the plastic optical fiber in a mixture of a 50 to 100 mM KOH solution in ethanol solvent, an NiSO$_4$ solution in ethanol solvent and glutaraldehyde or succinaldehyde. The formyl groups thus introduced on the core surface are then bound to the amino group in the immunological substance to prepare a plastic optical fiber with the immunological substance immobilized thereto.

However, in the method of WO90/13029, since a dialdehyde is used to carry out the reaction in introducing formyl groups on a core surface of the optical fiber, the optical fiber is likely to have a polymeric structure formed thereon. As a result, the core surface of the optical fiber tends to have turbidity. A problem has been pointed out that this turbidity results in increased transmission losses of fluorescence when the optical fiber is used for fluoroimmunoassay, etc.

SUMMARY OF THE INVENTION

An object of the present invention is to provide a method for producing an optical fiber having formyl groups on a core surface thereof wherein turbidity on the core surface is minimized to reduce the transmission losses of light and formyl groups are easily and industrially advantageously introduced on the core surface.

In order to solve this problem, the inventors have made extensive investigations and found that the above problems can be solved by the following two embodiments.

First, taking note of the fact that the alkali metal hydroxide concentration in the treating solution used to introduce formyl groups on a surface of an optical fiber unexpectedly affects the degree of glutaraldehyde polymerization and hence the amount of formyl groups introduced on the core surface of the optical fiber, the inventors have developed a method using a treating solution having no such effects (first embodiment). Specifically, the inventors have established optimum conditions for introduction of formyl groups by specifying various factors such as the concentrations of the compound having formyl groups and of the Ni salt, alkali metal hydroxide, the choice of alcohol or water, and the reaction time and temperature.

Next, in view of the fact that the use of such a treating solution in the first embodiment using a dialdehyde results in a limited range of optimum conditions, though polymerization of glutaraldehyde, etc. can be prevented, the inventors have developed other methods for introducing formyl groups which are the binding group to the immunological substances (second embodiment) including:

[1] A method comprising introducing a vic-diol group on a core surface of the optical fiber, and then oxidizing it to introduce formyl groups on the core surface;

[2] A method comprising introducing a primary hydroxyl group, and then oxidizing it to introduce formyl groups on the core surface; and

[3] A method comprising introducing an alkenyl group, and then oxidizing it to introduce formyl groups on the core surface.

Accordingly, the gist of the present invention is as follows:

(1) A method for producing a plastic optical fiber having formyl groups on a core surface thereof, comprising the step of immersing the core surface of the plastic optical fiber in a treating solution containing at least a 0.5 to 40 mM alkali metal hydroxide and a compound having formyl groups in water or lower alcohol solvent to introduce formyl groups on the core surface (first embodiment);

(2) A method for producing a plastic optical fiber having formyl groups on a core surface thereof, comprising the steps of reacting the core surface of the plastic optical fiber with a compound represented by Formula (3):

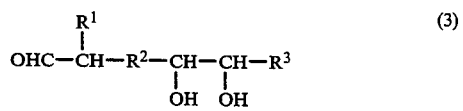

wherein $R^1$ represents a hydrogen atom, a lower alkyl group of $C_1$ to $C_3$ or a hydroxyl group; $R^2$ represents $-(CH_2)_n-$ and n represents an integer of 0 to 6; and $R^3$ represents a hydrogen atom or an alkyl group of $C_1$ to $C_6$, to introduce on the core surface a vic-diol group represented by Formula (4):

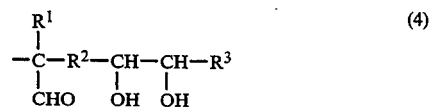

wherein $R^1$, $R^2$ and $R^3$ are the same as above, and then oxidizing the vic-diol group to introduce formyl groups on the core surface (second embodiment [1]);

(3) A method for producing a plastic optical fiber having formyl groups on a core surface thereof, comprising the steps of reacting the core surface of the plastic optical fiber with a primary aldehyde alcohol to introduce a primary hydroxyl group on the core surface, and then oxidizing the primary hydroxyl group to introduce formyl groups on the core surface (second embodiment [2]); and (4) A method for producing a plastic optical fiber having formyl groups on a core surface thereof, comprising the steps of reacting the core surface of the plastic optical fiber with a compound represented by Formula (6):

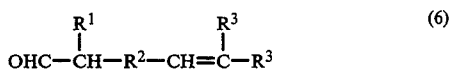

wherein $R^1$ represents a hydrogen atom, a lower alkyl group of $C_1$ to $C_3$ or a hydroxyl group; $R^2$ represents $-(CH_2)_n-$ and n represents an integer of 0 to 6; and $R^3$ represents a hydrogen atom or an alkyl group of $C_1$ to $C_6$, to introduce on the core surface an alkenyl group represented by Formula (7):

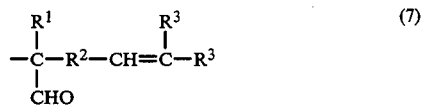

wherein $R^1$, $R^2$ and $R^3$ are the same as above, and then oxidizing the alkenyl group to introduce formyl groups on the core surface (second embodiment [3]).

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 1 is a graph showing the relationship between the amount of enzyme immobilized on the surface of an optical fiber and the KOH concentration in the treating solution;

Figure 2:
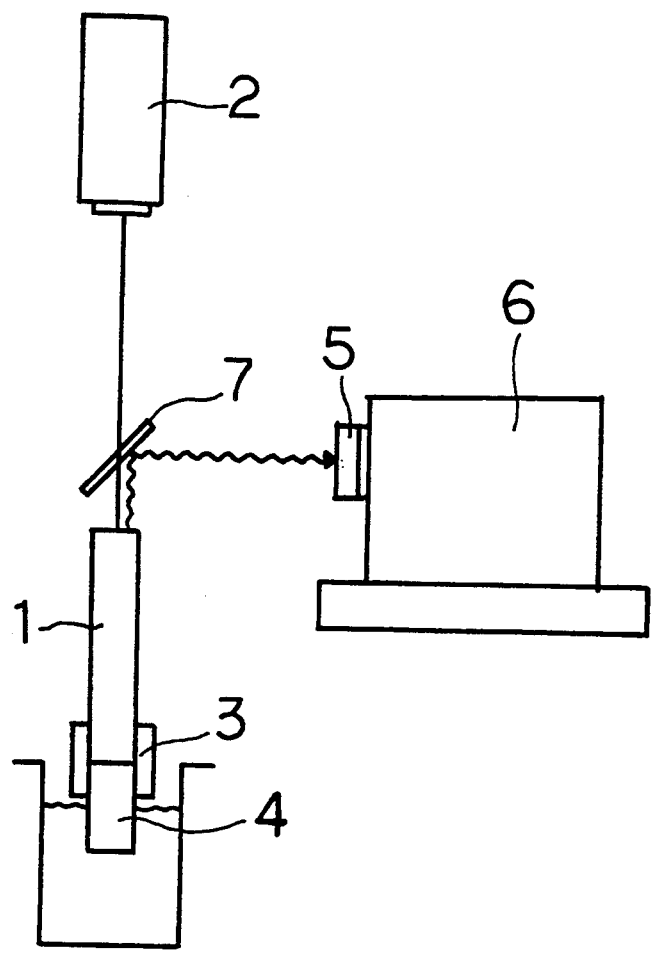
FIG. 2 is a schematic view of a single-laser fluorometric system.
Figure 3:
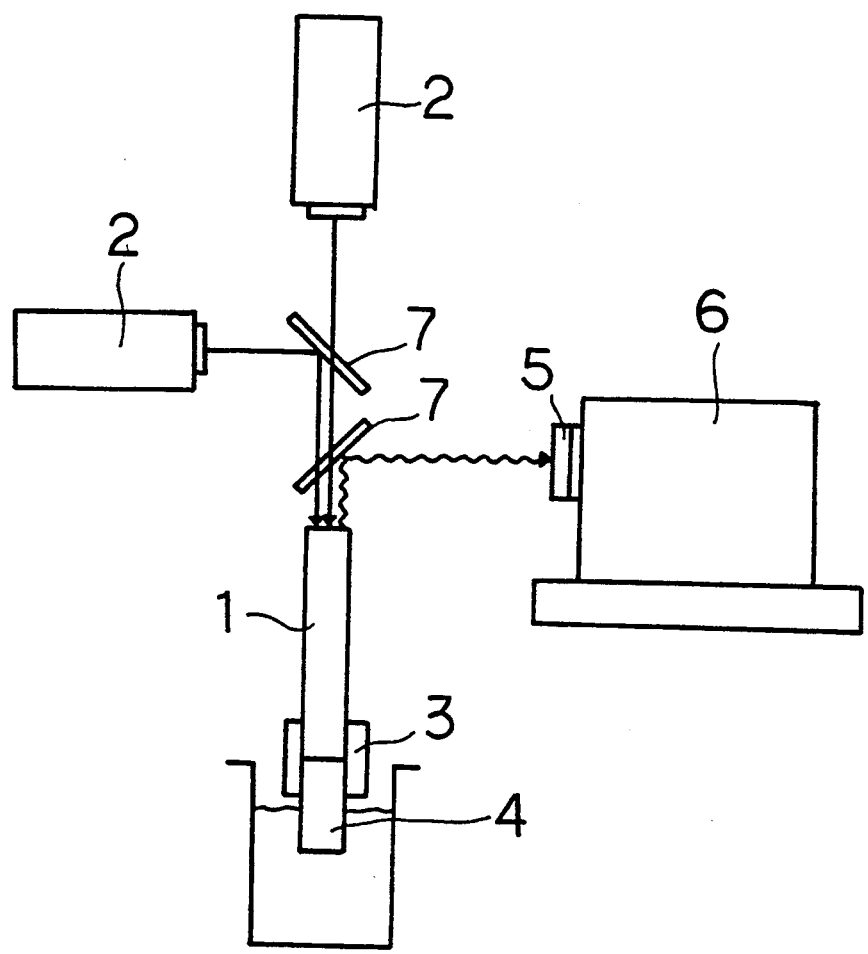
FIG. 3 is a schematic view of a double-laser fluorometric system.

The reference numerals in FIGS. 1 through 3 denote the following elements:

Element 1 is an optical fiber, element 2 a laser, element 3 a guide rail for optical axis alignment, element 4 a sensing chip, element 5 a filter, element 6 a fluorescence detector and element 7 a half mirror.

DETAILED DESCRIPTION OF THE INVENTION

The optical fibers used in the present invention are plastic optical fibers. Although the resins constituting the plastic optical fibers are not particularly limitative, they are required to be materials which do not adsorb the immunological substances and have good light transmittance, and examples thereof include polystyrene, polyacrylic ester, polyester, polyacrylamide, polyvinyl alcohol, polyethylene terephthalate, polycarbonate, and copolymers thereof. Among them, a preference is given to the polyacrylic ester. The polyacrylic ester is an acrylic resin having an ester structure, and examples thereof include synthetic resins comprising polymers of ester derivatives of acrylic acid, methacrylic acid, etc., specifically polymers of methyl acrylate, ethyl acrylate, methyl methacrylate, etc. Among these polyacrylic esters, one particularly suitably used in the present invention is polymethyl methacrylate. This is because the polymethyl methacrylate is superior to other resins particularly in light transmittance.

Also, the plastic optical fibers which can be used in the present invention may be, for example, copolymers of a monomer such as methyl acrylate, ethyl acrylate, methyl methacrylate, etc. with a monomer such as styrene, etc.

In the production method of the present invention, when the surface of the optical fibers described above is treated, it is desired that the core surface is exposed by stripping the clad layer of the optical fibers. The reason therefor is that since the optical fibers usually have only a diameter of 1 mm and the diameter of the core section is about 0.97 mm (sectional area is 0.739 mm$^2$), it is necessary to increase the core surface area by stripping the clad layer in order to introduce a large number of formyl groups. Also, it is desired that the end surface of the optical fibers is polished, and the polishing is preferably carried out by using an alcohol as a lubricant.

The method of the present invention will be described in further detail by means of each of the following embodiments.

FIRST EMBODIMENT

The method in the first embodiment of the present invention comprises the step of immersing the core surface of the plastic optical fiber in a treating solution containing at least a 0.5 to 40 mM alkali metal hydroxide and a compound having formyl groups in water or lower alcohol solvent to introduce formyl groups on the core surface.

The water or lower alcohol used in this embodiment is at least one kind selected from the group consisting of water, methanol, ethanol, propanol and butanol, with a preference given to water or ethanol. In this embodiment, a solution of alkali metal hydroxide in such water or lower alcohol solvent is used. The alkali metal hydroxide is at least one kind selected from the group consisting of potassium hydroxide, sodium hydroxide and lithium hydroxide, with a preference given to potassium hydroxide. The alkali metal hydroxide concentration is 0.5 to 40 mM, preferably 13 to 27 mM. Alkali metal hydroxide concentrations not falling in this range are undesirable, since alkali metal hydroxide concentrations of lower than 0.5 mM result in considerably reduced amounts of formyl groups introduced thereon, and since alkali metal hydroxide concentrations exceeding 40 mM, particularly 50 mM, tend to result in polymerization of compounds having formyl groups such as glutaraldehyde. As seen in FIG. 1, which shows the relationship between the amount of enzyme immobilized on the surface of an optical fiber and the KOH concentration in the treating solution, KOH concentrations of lower than 0.5 mM result in remarkably reduced amounts of enzyme immobilized, and KOH concentrations exceeding 50 mM result in significant fluctuation in the amount of enzyme immobilized according to the change in KOH concentration.

The compound having formyl groups which is used in this embodiment is represented by Formula (2):

wherein $R^1$ represents a hydrogen atom, a lower alkyl group of $C_1$ to $C_3$ or a hydroxyl group; and $R^2$ represents $—(CH_2)_n—$ and n represents an integer of 0 to 6.

In this case, the lower alkyl group of $C_1$ to $C_3$ represented by $R^1$, whether straight-chained or branched, is exemplified by methyl, ethyl, propyl and isopropyl. n in $R^2$ is an integer of 0 to 6, preferably 1 to 4. Such compounds, for example, include glutaraldehyde, succinaldehyde, and the like, with a preference given to glutaraldehyde. It is advantageous that $R^1$ is a hydroxyl group, since it suppresses formyl group polymerization.

The treating solution used in this embodiment is prepared by mixing at least a 0.5 to 40 mM alkali metal hydroxide solution in water or lower alcohol solvent and a compound having formyl groups. Preferably, an Ni salt solution is additionally mixed. The Ni salt solution used in this embodiment is prepared by dissolving an Ni salt such as $NiSO_4$ or $NiCl_2$ in water or a saturated solution of lower alcohol as described above, with a preference given to an $NiSO_4$ solution. Although the alcohol used to prepare a saturated Ni solution is not subject to limitation, ethanol is preferably used.

In this embodiment, the concentration of the compound having formyl groups in the treating solution is normally 0.2 to 1M. This is because concentrations of lower than 0.2M result in lower amounts of formyl groups introduced thereon, and because concentrations exceeding 1M result in surface turbidity due to polymerization reaction of the compounds. In the case of adding Ni salt to the treating solution, its concentration in the mixture is normally not higher than 0.9 mM, preferably at least not lower than about 0.01 mM.

In the method for producing the optical fiber of the present invention, polymerization of compounds having formyl groups, such as glutaraldehyde, is suppressed by carrying out the reaction while immersing a core surface of an optical fiber in the treating solution prepared as described above, thereby introducing formyl groups on the core surface. Thus obtained optical fiber presumably has on the surface thereof a structure represented by Formula (1):

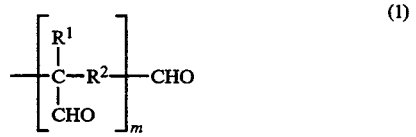

wherein $R^1$ represents a hydrogen atom, a lower alkyl group of $C_1$ to $C_3$ or a hydroxyl group; $R^2$ represents $—(CH_2)_n—$ and n represents an integer of 0 to 6; and m represents 1.

In other words, the optical fiber presumably having on the surface thereof a structure wherein m is 1 is obtained by this method.

It is, therefore, possible to produce an optical fiber having formyl groups introduced thereon characterized by little transmission losses of light and little fluctuation in the amount of formyl groups introduced on a core surface of the optical fiber.

In this case, the reaction is achieved while conducting a heat treatment within the temperature range of normally from 45° C. to 60° C. for a period of normally 5 to 20 minutes. The heat treatment is normally followed by washing with dilute hydrochloric acid and phosphate-buffered saline.

SECOND EMBODIMENT

In the present invention, the method for introducing formyl groups on the core surface of the optical fibers according to the second embodiment, as described above, may be as follows:

[1] A method comprising introducing a vic-diol group on a core surface of the optical fiber, and then oxidizing it to introduce formyl groups on the core surface;

[2] A method comprising introducing a primary hydroxyl group, and then oxidizing it to introduce formyl groups on the core surface; and

[3] A method comprising introducing an alkenyl group, and then oxidizing it to introduce formyl groups on the core surface.

Each of these methods are described in details below in the above order.

1) Method via vic-diol group

In this embodiment, the compound to be reacted with an optical fiber to introduce a vic-diol group is exemplified by a compound represented by Formula (3):

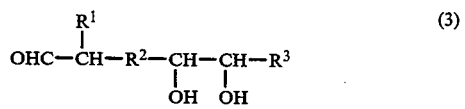

wherein $R^1$ and $R^2$ are the same as above; and $R^3$ represents a hydrogen atom or an alkyl group of $C_1$ to $C_6$.

The groups represented by $R^1$ and $R^2$ are exemplified by the same groups as specified above. The alkyl group of $C_1$ to $C_6$ represented by $R^3$ is exemplified by methyl group, ethyl group, propyl group, isopropyl group, butyl group, pentyl group and hexyl group.

Specific examples of the compounds represented by Formula (3) described above include 3,4-dihydroxybutanal and 4,5-dihydroxypentanal.

The reaction between the optical fiber and the compound represented by Formula (3) is achieved by adding the compound of Formula (3) to a 50 to 100 mM KOH solution in water or lower alcohol solvent to a final concentration of 0.1 to 1M, and immersing the optical fiber in this solution at 45° to 60° C. for 5 to 20 minutes. After completion of the reaction, the optical fiber is washed with distilled water, ethanol, etc.

This operation makes it possible to introduce on the core surface of the plastic optical fiber a vic-diol group represented by Formula (4):

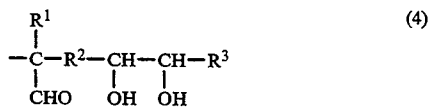

wherein $R^1$, $R^2$ and $R^3$ are the same as above.

In this embodiment, the vic-diol group moiety thus obtained may be oxidized to a formyl group.

Examples of oxidants include metaperiodic acid, alkali metal salts thereof and lead tetraacetate, with a preference given to sodium metaperiodate.

The oxidation reaction is achieved by, for example, immersing the optical fiber in a 0.1 to 5M aqueous solution of sodium metaperiodate for 1 to 6 hours under ice-cooling conditions. After completion of the reaction, the optical fiber is washed with distilled water, etc.

2) Method via primary hydroxyl group

In this embodiment, the introduction of formyl groups on a core surface of a plastic optical fiber is achieved by first reacting the core surface with a primary aldehyde alcohol to introduce a primary hydroxyl group thereon, and then oxidizing the primary hydroxyl group to a formyl group.

The primary aldehyde alcohol to be reacted with a plastic optical fiber to introduce a primary hydroxyl group on a core surface thereof is represented by Formula (5):

$$OHC-\underset{\underset{R^1}{|}}{CH}-R^2-CH_2OH \qquad (5)$$

wherein $R^1$ and $R^2$ are the same as above.

The groups represented by $R^1$ and $R^2$ in this embodiment are exemplified by the same groups as specified above.

In this embodiment, any compound can be used without limitation, as long as it is represented by the above formula. However, it is preferable to select a compound such as 3-hydroxypropanal, 4-hydroxybutanal, 5-hydroxypentanal, 6-hydroxyhexanal, 7-hydroxyheptanal, 8-hydroxyoctanal, 4-hydroxy-3-methylbutanal or 4-ethyl-6-hydroxyhexanal.

The binding reaction between a core surface of the plastic optical fiber and the primary aldehyde alcohol is carried out under heating conditions in alkaline alcohol or water. For example, the reaction is carried out by immersing a core surface of the plastic optical fiber in a treating solution prepared by dissolving a primary aldehyde alcohol in an alkali metal hydroxide solution in lower alcohol solvent or water, heating it for a given period of time and then washing the optical fiber with distilled water, etc.

The lower alcohol used in this embodiment is at least one kind selected from the group consisting of methanol, ethanol, propanol and butanol, with a preference given to ethanol. In this embodiment, a solution of alkali metal hydroxide in such a lower alcohol solvent or water is used. The alkali metal hydroxide is at least one kind selected from the group consisting of potassium hydroxide, sodium hydroxide and lithium hydroxide, with a preference given to potassium hydroxide. The alkali metal hydroxide concentration is 0.5 to 100 mM, preferably 20 to 50 mM.

The treating solution used in this embodiment is prepared by mixing alkali metal hydroxide solution in a lower alcohol solvent and a primary aldehyde alcohol. Preferably, an Ni salt solution is additionally mixed. The Ni salt solution used in this embodiment is prepared by dissolving an Ni salt such as $NiSO_4$ or $NiCl_2$ in water or a saturated solution of lower alcohol as described above, with a preference given to an $NiSO_4$ solution. Although the lower alcohol is not subject to limitation, ethanol is preferably used.

In this embodiment, the concentration of the primary aldehyde alcohol in the treating solution is normally not lower than 0.2M. This is because concentrations of lower than 0.2M result in lower amount of primary hydroxyl groups introduced thereon. In the case of adding Ni salt to the treating solution, its concentration in the mixture is normally not higher than 0.9 mM, preferably at least not lower than about 0.01 mM.

The reaction is proceeded by carrying out a heat treatment at a temperature range of normally 45° to 60° C. for a period of normally 5 to 20 minutes. The heat treatment is normally followed by washing with distilled water, etc.

The primary hydroxyl group thus introduced on a core surface of the plastic optical fiber can be oxidized to a formyl group. Examples of oxidants which can be used here include pyridinium chlorochromate (PCC) and pyridinium dichromate (PDC).

When using PCC or PDC, an optical fiber having a primary hydroxyl group thereon is immersed in a 1 to 20% PCC or PDC solution in distilled water solvent at 4° C. to room temperature for 0.5 to 8 hours, after which it is washed with 1 to 20 mM dilute hydrochloric acid or dilute sulfuric acid and water. This treatment makes it possible to oxidize the primary hydroxyl group to a formyl group and introduce formyl groups on a core surface.

3) Method via alkenyl group

In this embodiment, the method of introducing formyl groups on a core surface of a plastic optical fiber comprises the step of first reacting the core surface of the plastic optical fiber with a compound represented by Formula (6):

$$OHC-\underset{\underset{R^1}{|}}{CH}-R^2-CH=\underset{\underset{R^3}{|}}{C}-R^3 \qquad (6)$$

wherein $R^1$, $R^2$ and $R^3$ are the same as above, thereby introducing on the core surface an alkenyl group represented by Formula (7):

$$-\underset{\underset{CHO}{|}}{\overset{\overset{R^1}{|}}{C}}-R^2-CH=\underset{\underset{R^3}{|}}{C}-R^3 \qquad (7)$$

wherein $R^1$, $R^2$ and $R^3$ are the same as above.

Examples of $R^1$, $R^2$ and $R^3$ are exemplified by the same groups as specified above. A compound represented by Formula (6) is prepared by a known method. For example, it can easily be prepared by reacting with pyridinium chlorochromate in dichloromethane solvent at room temperature a compound represented by Formula (8):

$$HOCH_2-\underset{\underset{R^1}{|}}{CH}-R^2-CH=\underset{\underset{R^3}{|}}{C}-R^3 \qquad (8)$$

wherein $R^1$, $R^2$ and $R^3$ are the same as above.

As for the compounds thus obtained represented by Formula (6), those such as 3-buten-1-al, 3-penten-1-al, 4-penten-1-al, 3-hexen-1-al, 5-hexen-1-al, 6-hepten-1-al, 5-methyl-3-hexen-1-al, 7-octen-1-al, 8-decen-1-al and 3-ethyl-6-octen-1-al are preferably used.

To introduce formyl groups on a core surface of a plastic optical fiber, the core surface is reacted with the compound thus obtained represented by Formula (6) as described above, thereby binding to the core surface an alkenyl group represented by Formula (7):

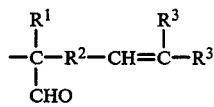

wherein $R^1$, $R^2$ and $R^3$ are the same as above.

In introducing this alkenyl group, a compound represented by Formula (6) and the core of a plastic optical fiber are heated in alkaline alcohol or water.

The lower alcohol used in this embodiment is at least one kind selected from the group consisting of methanol, ethanol, propanol and butanol, with a preference given to ethanol. In this embodiment, a solution of alkali metal hydroxide in such a lower alcohol solvent or water is used. The alkali metal hydroxide is at least one kind selected from the group consisting of potassium hydroxide, sodium hydroxide and lithium hydroxide, with a preference given to potassium hydroxide.

The treating solution for introducing the alkenyl group represented by Formula (7) used in this embodiment is prepared by mixing 0.5 to 100 mM of alkali metal hydroxide solution in water or lower alcohol solvent and a compound represented by Formula (6). Preferably, an Ni salt solution is additionally mixed. The Ni salt solution used in this embodiment is prepared by dissolving an Ni salt such as $NiSO_4$ or $NiCl_2$ in water or a saturated solution of lower alcohol as described above, with a preference given to an $NiSO_4$ solution. Although the lower alcohol is not subject to limitation, ethanol is preferably used.

To convert the alkenyl group represented by Formula (7) thus introduced on a core surface of the plastic optical fiber to a formyl group, two methods are available: One method wherein the alkenyl group is converted directly to a formyl group by ozonolysis and the other method wherein the alkenyl group is converted to a formyl group via a vic-diol group by osmium tetroxide-metaperiodate treatment.

(a) Ozonolysis is carried out as follows: First, a plastic optical fiber having an alkenyl group represented by Formula (7) is immersed in water or a lower alcohol such as ethanol at 0° C. to room temperature, and a mixed gas stream of oxygen and 0.1 to 20% ozone is sparged to the solution for 0.1 to 24 hours. The optical fiber is then washed with fresh water or a lower alcohol such as ethanol to yield the desired plastic optical fiber having formyl groups.

(b) The oxidation method via a vic-diol group is carried out as follows: First, a plastic optical fiber having an alkenyl group represented by Formula (7) is immersed in a 1 to 5 mg/ml aqueous solution of osmium tetroxide at room temperature for 12 to 24 hours to convert the alkenyl group to a vic-diol group.

The optical fiber is then taken out from the solution and washed with distilled water, after which it is immersed in an ice-cooled 0.1 to 5M aqueous solution of metaperiodate for 0.5 to 2 hours under ice cooling conditions and then taken out from the solution and washed with distilled water, etc. to yield the desired plastic optical fiber having formyl groups on the core surface thereof. The preferable metaperiodate used for this purpose is sodium metaperiodate.

By this second embodiment, as in the same as the first embodiment, there can be obtained an optical fiber presumably having on the surface thereof a structure represented by Formula (1):

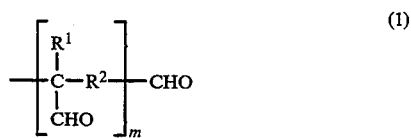

wherein $R^1$ represents a hydrogen atom, a lower alkyl group of $C_1$ to $C_3$ or a hydroxyl group; $R^2$ represents $—(CH_2)_n—$ and n represents an integer of 0 to 6; and m represents 1.

By immersing the core surface of an optical fiber on which formyl groups have been introduced by the first or second embodiment in an aqueous solution of an antigen or antibody having an amino group at 4° to 25° C., the antigen or antibody is bound by means of an imide bond to immobilize thereon. Specifically, an immunological substance required to assay the antigen or antibody is immobilized on the surface of the optical fiber, and such an optical fiber in the present invention is then used in a fluoroimmunoassay, etc. for biomaterials.

According to the method for producing the optical fiber of the present invention, turbidity on the core surface of the optical fiber due to polymerization of dialdehyde as seen in conventional methods can be prevented. Use of the optical fiber in a fluoroimmunoassay, therefore, makes it possible to conduct high-sensitive immunoassay, since a 100% optical transmission is maintained with little transmission losses of fluorescence.

EXAMPLES

The present invention is hereinafter described in more detail by means of the following working examples and comparative examples, which are not to be construed as limitative.

EXAMPLE 1

Assay of Human Pancreatic Amylase Antibody (1) First, 4 mg of $Na_2CO_3$ and 10 mg of biotin were dissolved in 100 μl of water. This solution was mixed with 2 ml of a 1.8 μM chitosan solution, and 100 mg of water-soluble carbodiimide was added, followed by an overnight reaction at room temperature. To this reaction mixture, 4 ml of a mixture of 0.2 g/ml $Na_2CO_3$ and 0.1 g/ml NaCl was added to precipitate biotinylated chitosan (b-c). After recovery by centrifugation, this precipitate was twice washed with a mixture of 0.1 g/ml $Na_2CO_3$ and 0.3 g/ml NaCl and then suspended in 2 ml of 10 mM phosphate buffer (pH 7), followed by overnight dialysis against 500 ml of the same buffer at 4° C. After completion of the dialysis, the dialyzate was recovered to yield a b-c suspension.

(2) To the b-c suspension in the above (1), 100 μg of anti-human Ig antibody from goat and then 10 mg of water-soluble carbodiimide were added, followed by a reaction at 4° C. for 6 hours. After completion of the reaction, the unreacted substances were removed using an anion exchange column to yield b-c with anti-human Ig antibody bound thereto.

(3) 1 mg of avidin and 0.2 ml of triethylamine were dissolved in 1 ml of ethanol. To this solution was added NK1160 (a cyanine dye produced by Japanese Research Institute for Photosensitizing Dyes Co., Ltd.). After the dye was dissolved, 0.3 ml of dicyclohexylcarbodiimide was added, followed by an overnight reaction at room temperature.

(4) After the avidin was centrifugally precipitated and recovered, the precipitate was twice washed with ethanol and centrifuged, after which the ethanol remaining in the precipitate was removed under reduced pressure using an aspirator. This residue was dissolved in 20 mM acetate buffer (pH 6.5) to yield an avidin modified with NK1160.

(5) A plastic optical fiber made of polymethyl methacrylate (produced by Mitsubishi Rayon Co., Ltd.) was cut into a 3 cm piece. Both ends were polished with a polishing film, using ethanol as a lubricant.

(6) 10 mg of $NiSO_4$ was dissolved in 0.5 ml of water, and 2.5 ml of ethanol was added. The resulting precipitate was removed by centrifugation, and the supernatant collected was used as an Ni-ethanol solution. To 0.4 ml of a 20 mM KOH solution in ethanol solvent, 0.1 ml of the Ni-ethanol solution and 50 µl of 50% glutaraldehyde were mixed to yield a treating solution (14.5 mM KOH, 0.45M glutaraldehyde, 0.47 mM Ni salt).

(7) A surface of the optical fiber in the above (5) was immersed in the treating solution in the above (6) at 50° C. for 10 minutes, after which it was washed with 20 mM hydrochloric acid and then phosphate-buffered saline (PBS) to introduce formyl groups on the core surface of the optical fiber. This optical fiber was then immersed in a 2 mg/ml human pancreatic amylase solution at 4° C. overnight.

(8) The optical fiber was taken out from the solution and immersed in a 1% aqueous $NaBH_4$ solution for 15 minutes, after which it was washed with PBS to yield a sensor with human pancreatic amylase immobilized thereto, which was used as a sensing chip.

(9) In a given amount of a known concentration of a human pancreatic amylase solution, the sensing chip in the above (8) was immersed for 20 minutes. The sensing chip was then immersed in the b-c solution in the above (2), which contained anti-human Ig antibody bound thereto, for 20 minutes. The sensing chip in the above (8) was further immersed for 5 minutes in the NK1160-modified avidin solution in the above (4).

(10) The sensing chip was washed with a 1M aqueous potassium isothiocyanate solution containing 0.2% Tween 20, after which it was excited with an He-Ne laser system using the single-laser fluorometric system illustrated in FIG. 2. Fluorescence could be detected up to 0.5 ng/ml.

COMPARATIVE EXAMPLE 1

When a sensing chip made with a 50 mM KOH solution for the treating solution of Example 1 (6) was used, the human pancreatic amylase antibody could be detected only up to 20 ng/ml.

EXAMPLE 2

(1) A biotinylated chitosan with anti-human Ig antibody bound thereto was obtained in the same manner as in Example 1 (1) and (2).

(2) An NK1160-modified avidin was obtained in the same manner as in Example 1 (3) and (4).

(3) 10 mg of $NiSO_4$ was dissolved in 3.0 ml of water to yield an aqueous Ni solution. To 0.4 ml of a 20 mM aqueous KOH solution, 0.1 ml of the aqueous Ni solution and 50 µl of 50% glutaraldehyde were added to yield a treating solution (14.5 mM KOH, 0.45M glutaraldehyde, 0.47 mM Ni salt).

(4) A surface of the optical fiber prepared in the same manner as in Example 1 (5) was immersed in the treating solution in the above (3) at 50° C. for 10 minutes, after which it was washed with 20 mM hydrochloric acid and then with phosphate-buffered saline (PBS) to introduce formyl groups on the core surface of the optical fiber. This optical fiber was then immersed in a 2 mg/ml human pancreatic amylase solution at 4° C. overnight.

(5) The optical fiber was taken out from the solution and immersed in a 1% aqueous $NaBH_4$ solution for 15 minutes, after which it was washed with PBS to yield a sensor with human pancreatic amylase immobilized thereto, which was used as a sensing chip.

(6) Next, the human pancreatic amylase antibody was assayed in the same manner as in Example 1 (9) and (10). The antibody could be detected up to 0.5 ng/ml.

EXAMPLE 3

When the concentration of KOH used to prepare the treating solution of Example 1 (6) was changed over the range of ±10% (18 to 22 mM), human pancreatic amylase could be detected up to 0.5 ng/ml with high reproducibility.

COMPARATIVE EXAMPLE 2

When the concentration of KOH used to prepare the treating solution of Comparative Example 1 was changed over the range of ±10% (45 to 55 mM), detection of human pancreatic amylase varied within the range of from 8 to 42 ng/ml.

EXAMPLE 4

Assay of Human Pancreatic Amylase Antibody (1) A b-c suspension was obtained in the same manner as in Example 1 (1).

(2) A b-c suspension with human pancreatic amylase antibody bound thereto was obtained in the same manner as in Example 1 (2) except that a human pancreatic amylase antibody from mouse was used in place of the anti-human antibody.

(3) An NK1160-modified avidin was obtained in the same manner as in Example 1 (3) and (4).

(4) A plastic optical fiber and a treating solution containing dialdehyde were prepared in the same manner as in Example 1 (5) and (6), except that the treating solution was prepared with a commercial product of 2-hydroxy-4-formyl-butanal [$OHC—CH(OH)—CH_2CH_2—CHO$], 10 mM NaOH alkali metal hydroxide and a 3:1 methanol-propanol mixture solvent.

(5) A sensor with human pancreatic amylase immobilized thereto was prepared in the same manner as in Example 1 (7) and (8), and this sensor was used as a sensing chip.

(6) In a given amount of a known concentration of a human pancreatic amylase antibody solution, a given amount of the b-c suspension in the above (2), which contained the human pancreatic amylase antibody bound thereto, was added, and the sensing chip in the above (5) was immersed for 20 minutes. The sensing chip was then immersed in the NK1160-modified avidin solution in the above (3) for 5 minutes.

(7) Next, the human pancreatic amylase antibody was assayed in the same manner as in Example 1 (10). The antibody could be detected up to 0.5 ng/ml.

EXAMPLE 5

Assay of hCG (1) 100 μg of human chorionic gonadotropin (hCG) and 2 mg of biotin were dissolved in 1 ml of 20 mM borate buffer (pH 8), and 10 mg of water-soluble carbodiimide (CHMC) was added, followed by an overnight reaction at 4° C. After completion of the reaction, the reaction product was subjected to ion exchange chromatography to separate a purified biotinylated hCG solution.

(2) 1 mg of avidin and 0.2 ml of triethylamine were dissolved in 1 ml of ethanol. Next, 1.8 mg of fluorescein isothiocyanate (fluorescein) was dissolved in the solution, followed by a reaction at room temperature under shading conditions for 6 hours. After the solvent was removed under reduced pressure from the reaction solution, the residue was suspended in 1 ml of 50 mM acetate buffer (pH 4.5). After this suspension was mixed with the biotinylated hCG solution in the above (1), the mixture was subjected to gel filtration to separate a purified solution of biotinylated hCG and fluorescein labelled avidin (f-hCG).

(3) A sensor with hCG antibody immobilized thereto was prepared in the same manner as in Example 1 (5) through (8) except that the hCG antibody was used in place of human pancreatic amylase, and that the treating solution containing dialdehyde was prepared with a commercial product of 2-ethyl-5-formyl-pentanal [OH-C—CH($C_2H_5$)—$CH_2CH_2CH_2$—CHO], LiOH alkali metal hydroxide and butanol solvent, and this sensor was used as a sensing chip.

(4) To each concentration of hCG solution sample, a given amount of the f-hCG solution in the above (2) was added. In this mixture, the sensing chip in the above (3) was immersed at room temperature for 30 minutes, after which it was washed with PBS containing Tween 20.

(5) The sensing chip in the above (4) was immersed in a 1% sodium carbonate solution, and it was irradiated with semiconductor laser beams of 780 nm and 1360 nm to measure fluorescence at 518 nm, using the double-laser fluorometric system illustrated in FIG. 3. The target substance hCG could be detected up to 0.4 ng/ml.

COMPARATIVE EXAMPLE 3

When a sensing chip made with a 0.5 mM LiOH solution for the reaction in Example 4 (3) was used to assay hCG in the same manner, hCG could be detected only up to 12 ng/ml.

EXAMPLE 6

(1) A plastic optical fiber made of polymethyl methacrylate (produced by Mitsubishi Rayon Co., Ltd.) was cut into a 3 cm piece. Both ends were polished with a polishing film, using ethanol as a lubricant.

(2) 40 mg of 3,4-dihydroxybutanal was dissolved in 0.5 ml of a 20 mM KOH solution in ethanol solvent. In this solution, the optical fiber in the above (1) was immersed at 50° C. for 10 minutes with heating, after which the optical fiber was thoroughly washed with distilled water.

(3) 4 g of sodium metaperiodate was dissolved in 50 ml of water, and the optical fiber in the above (2) was immersed therein under ice cooling conditions for 1 hour. After completion of the reaction, the optical fiber was washed with water and phosphate buffered saline (PBS) and then immersed in a 2 mg/ml human pancreatic amylase solution at 4° C. overnight. The optical fiber was then washed with PBS containing 0.05% Tween (Tween PBS) to yield a sensor with human pancreatic amylase immobilized thereto, which was used as a sensing chip.

(4) 4 mg of $Na_2CO_3$ and 10 mg of biotin were dissolved in 100 μl of water. This solution was mixed with 2 ml of a 1.8 μM chitosan solution, and 100 mg of water-soluble carbodiimide was added thereto, followed by an overnight reaction at room temperature. To this reaction mixture, 4 ml of a mixture of 0.2 g/ml $Na_2CO_3$ and 0.1 g/ml NaCl was added to precipitate biotinylated chitosan (b-c). After recovery by centrifugation, this precipitate was twice washed with a mixture of 0.1 g/ml $Na_2CO_3$ and 0.3 g/ml NaCl and then suspended in 2 ml of 10 mM phosphate buffer (pH 7), followed by overnight dialysis against 500 ml of the same buffer at 4° C. After completion of the dialysis, the dialyzate was recovered to yield a b-c suspension.

(5) To the b-c suspension in the above (4), 100 μg of goat-derived anti-human Ig antibody and then 10 mg of water-soluble carbodiimide were added, followed by a reaction at 4° C. for 6 hours. After completion of the reaction, the unreacted substances were removed using an anion exchange column to yield b-c with anti-human Ig antibody from goat bound thereto.

(6) 1 mg of avidin and 0.2 ml of triethylamine were dissolved in 1 ml of ethanol. To this solution was added NK1160 (a cyanine dye produced by Japanese Research Institute for Photosensitizing Dyes Co., Ltd.). After the dye was completely dissolved, 0.3 ml of dicyclohexyl-carbodiimide was added, followed by an overnight reaction at room temperature.

(7) After the avidin was centrifugally precipitated and recovered, the precipitate was twice washed with ethanol and centrifugally recovered, after which the ethanol remaining in the precipitate was removed under reduced pressure using an aspirator. This residue was dissolved in 20 mM acetate buffer (pH 6.5) to yield an avidin modified with NK1160.

(8) In a given amount of a known concentration of a human pancreatic amylase solution, the sensing chip in the above (3) was immersed for 20 minutes. The sensing chip was washed with 1M aqueous potassium thiocyanate solution containing 0.2% Tween 20, after which it was immersed in the b-c solution, which contained anti-human Ig antibody from goat bound thereto, for 20 minutes. The sensing chip in the above (3) was further immersed for 5 minutes in the NK1160-modified avidin solution in the above (7).

(9) The sensing chip was further washed with Tween potassium thiocyanate, after which it was excited with a helium-neon laser system using the single-laser fluorometric system illustrated in FIG. 2. Fluorescence could be detected up to 0.4 ng/ml.

EXAMPLE 7

A human pancreatic amylase antibody was assayed in the same manner as in Example 6 except that 0.5 ml of 20 mM KOH aqueous solution was used in place of 0.5 ml of a 20 mM KOH solution in ethanol solvent in Example 6 (2). The antibody could be detected up to 0.4 ng/ml.

COMPARATIVE EXAMPLE 4

(1) An optical fiber was treated in the same manner as in Example 6 (2) except that 50 μl of 50% glutaraldehyde was added in place of 3,4-dihydroxybutanal and sodium metaperiodate treatment was not conducted (2) The resulting optical fiber was then immersed in a 2 mg/ml human pancreatic amylase solution at 4° C. overnight. Thereafter, it was washed with Tween PBS to yield a sensor with human pancreatic amylase immobilized thereto, which was used as a sensing chip.

(3) Assay was conducted in the same manner as in Example 6 (4) through (9). The target substance could be detected only up to 25 ng/ml due to turbidity on the optical fiber surface.

EXAMPLE 8

(1) A plastic optical fiber made of polymethyl methacrylate (produced by Mitsubishi Rayon Co., Ltd.) was cut into a 3 cm piece. Both ends were polished with a polishing film, using ethanol as a lubricant.

(2) 10 mg of $NiSO_4$ was dissolved in 0.5 ml of water, and 2.5 ml of ethanol was added. The resulting precipitate was removed by centrifugation, and the supernatant collected was used as an Ni-ethanol solution. To 0.4 ml of a 20 mM KOH solution in ethanol solvent, 0.1 ml of the Ni-ethanol solution and 50 μl of 3-hydroxypropanal were mixed to yield a treating solution.

(3) A surface of the optical fiber in the above (1) was immersed in the treating solution in the above (2) at 50° C. for 10 minutes, after which it was washed with distilled water to introduce a 3-hydroxypropyl group on the core surface of the optical fiber. This optical fiber was then immersed in 10% PCC at room temperature for hours to introduce formyl groups.

(4) The thus-treated optical fiber in the above was washed with 10 mM sulfuric acid, distilled water and PBS, after which it was immersed in a 2 mg/ml human pancreatic amylase solution at 4° C. overnight. After completion of the reaction, the optical fiber was washed with PBS containing 0.05% Tween (Tween PBS) to yield a sensor with human pancreatic amylase immobilized thereto, which was used as a sensing chip.

(5) 4 mg of $Na_2CO_3$ and 10 mg of biotin were dissolved in 100 μl of water. This solution was mixed with 2 ml of a 1.8 μM chitosan solution, and 100 mg of water-soluble carbodiimide was added, followed by an overnight reaction at room temperature. To this reaction mixture, 4 ml of a mixture of 0.2 g/ml $Na_2CO_3$ and 0.1 g/ml NaCl was added to precipitate biotinylated chitosan (b-c). After recovery by centrifugation, this precipitate was twice washed with a mixture of 0.1 g/ml $Na_2CO_3$ and 0.3 g/ml NaCl and then suspended in 2 ml of 10 mM phosphate buffer (pH 7), followed by overnight dialysis against 500 ml of the same buffer at 4° C. After completion of the dialysis, the dialyzate was recovered to yield a b-c suspension.

(6) To the b-c suspension in the above (5), 100 μg of goat-derived anti-human Ig antibody and then 10 mg of water-soluble carbodiimide were added, followed by a reaction at 4° C. for 6 hours. After completion of the reaction, the unreacted substances were removed using an anion exchange column to yield b-c with anti-human Ig antibody bound thereto.

(7) 1 mg of avidin and 0.2 ml of triethylamine were dissolved in 1 ml of ethanol. To this solution was added NK1160 (a cyanine dye produced by Japanese Research Institute for Photosensitizing Dyes Co., Ltd.). After the dye was completely dissolved, 0.3 ml of dicyclohexylcarbodiimide was added, followed by an overnight reaction at room temperature.

(8) After the avidin was centrifugally precipitated and recovered, the precipitate was twice washed with ethanol and centrifuged, after which the ethanol remaining in the precipitate was removed under reduced pressure using an aspirator. This residue was dissolved in 20 mM acetate buffer (pH 6.5) to yield an avidin modified with NK1160.

(9) In a given amount of a known concentration of a human pancreatic amylase solution, the sensing chip above (4) was immersed for 20 minutes. The sensing chip was washed with 1M aqueous potassium thiocyanate solution containing 0.2% Tween 20, after which it was immersed in the b-c solution, which contained anti-human Ig antibody bound thereto, for 20 minutes. The sensing chip in the above (4) was further immersed for 5 minutes in the NK1160-modified avidin solution in the above (8).

(10) The sensing chip was further washed with Tween potassium thiocyanate, after which it was excited with a helium-neon laser system using the single-laser fluorometric system illustrated in FIG. 2. Fluorescence could be detected up to 3 ng/ml.

EXAMPLE 9

Assay was performed in the same manner as in Example 8 (3) except that a 5% PDC solution was used in place of PCC solution. The target substance could be detected up to 3 ng/ml with high reproducibility.

EXAMPLE 10

Formyl groups were introduced on a core surface of an optical fiber in the same manner as in Example 8 (1) through (3) except that 5-hydroxypentanal was used in place of 3-hydroxypropanal in Example 8 (2). The optical fiber having formyl groups thus obtained was treated in the same manner as in Example 8 (4) through (10). The target substance could be detected up to 3 ng/ml.

EXAMPLE 11

(1) Formyl groups were introduced on a core surface of an optical fiber in the same manner as in Example 8 (1) through (3) except that 4-hydroxy-3-methylbutanal was used in place of 3-hydroxypropanal in Example 8 (2).

(2) Next, the human pancreatic amylase antibody was measured in the same manner as in Example 8 (4) through (10). The target substance could be detected up to 4 ng/ml.

EXAMPLE 12

(1) A plastic optical fiber made of polymethyl methacrylate (produced by Mitsubishi Rayon Co., Ltd.) was cut into a 3 cm piece. Both ends were polished with a polishing film, using ethanol as a lubricant.

(2) 10 mg of $NiSO_4$ was dissolved in 3 ml of water to yield an aqueous Ni solution. To 0.4 ml of a 20 mM aqueous KOH solution, 0.1 ml of the aqueous Ni solution and 50 μl of 3-hydroxypropanal were added to yield a treating solution.

(3) Next, a human pancreatic amylase antibody was assayed in the same manner as in Example 8 (3) through (10). The target substance could be detected up to 3 ng/ml.

COMPARATIVE EXAMPLE 5

An optical fiber was treated in the same manner as in Example 8 except that glutaraldehyde was used in place of 3-hydroxypropanal in Example 8 (2) and the optical fiber was not immersed in PCC in the above (3). When the optical fiber thus obtained having on a core surface thereof a dialdehyde group bound thereto was used for immunoassay in the same manner as in Example 8, turbidity occurred on the core surface, and the target substance could be detected only up to 30 ng/ml, indicating a reduced assay sensitivity.

EXAMPLE 13

(1) A plastic optical fiber made of polymethyl methacrylate (produced by Mitsubishi Rayon Co., Ltd.) was cut into a 3 cm piece. Both ends were polished with a polishing film, using ethanol as a lubricant.

(2) 10 mg of $NiSO_4$ was dissolved in 0.5 ml of water, and 2.5 ml of ethanol was added thereto. The resulting precipitate was removed by centrifugation, and the supernatant collected was prepared as an Ni-ethanol solution. To 0.4 ml of a 20 mM KOH solution in ethanol solvent, 0.1 ml of the Ni-ethanol solution and 50 $\mu$l of 50% 4-penten-1-al were added to yield a treating solution.

(3) A surface of the optical fiber in the above (1) was immersed in the treating solution in the above (2) at 50° C. for 10 minutes, after which it was washed with 20 mM hydrochloric acid and then phosphate-buffered saline (PBS) to introduce a 3-butenyl group on the core surface of the optical fiber. This optical fiber was then immersed in ethanol, and a mixed gas stream of oxygen and 5% ozone was sparged at room temperature for 2 hours. The optical fiber was then taken out from the ethanol and then washed with fresh ethanol to introduce formyl groups on the core surface of the optical fiber.

(4) The thus-treated optical fiber in the above was washed with distilled water and PBS, after which it was immersed in a 2 mg/ml human pancreatic amylase solution at 4° C. overnight. After completion of the reaction, the optical fiber was washed with PBS containing 0.05% Tween (Tween PBS) to yield a sensor with human pancreatic amylase immobilized thereto, which was used as a sensing chip.

(5) 4 mg of $Na_2CO_3$ and 10 mg of biotin were dissolved in 100 $\mu$l of water. This solution was mixed with 2 ml of a 1.8 $\mu$M chitosan solution, and 100 mg of water-soluble carbodiimide was added, followed by an overnight reaction at room temperature. To this reaction mixture, 4 ml of a mixture of 0.2 g/ml $Na_2CO_3$ and 0.1 g/ml NaCl was added to precipitate biotinylated chitosan (b-c). After recovery by centrifugation, this precipitate was twice washed with a mixture of 0.1 g/ml $Na_2CO_3$ and 0.3 g/ml NaCl and then suspended in 2 ml of 10 mM phosphate buffer (pH 7), followed by overnight dialysis against 500 ml of the same buffer at 4° C. After completion of the dialysis, the dialyzate was recovered to yield a b-c suspension.

(6) To the b-c suspension in the above (5), 100 $\mu$g of goat-derived anti-human Ig antibody and then 10 mg of water-soluble carbodiimide were added, followed by a reaction at 4° C. for 6 hours. After completion of the reaction, the unreacted substances were removed using an anion exchange column to yield b-c with anti-human Ig antibody bound thereto.

(7) 1 mg of avidin and 0.2 ml of triethylamine were dissolved in 1 ml of ethanol. To this solution was added NK1160 (a cyanine dye produced by Japanese Research Institute for Photosensitizing Dyes Co., Ltd.). After the dye was completely dissolved, 0.3 ml of dicyclohexylcarbodiimide was added, followed by an overnight reaction at room temperature.

(8) After the avidin was centrifugally precipitated and recovered, the precipitate was twice washed with ethanol and centrifuged, after which the ethanol remaining in the precipitate was removed under reduced pressure using an aspirator. This residue was dissolved in 20 mM acetate buffer (pH 6.5) to yield an avidin modified with NK1160.

(9) In a given amount of a known concentration of a human pancreatic amylase solution, the sensing chip in the above (4) was immersed for 20 minutes. The sensing chip was washed with 1M aqueous potassium thiocyanate solution containing 0.2% Tween 20, after which it was immersed in the b-c solution, which contained anti-human Ig antibody bound thereto, for 20 minutes. The sensing chip in the above (4) was further immersed for 5 minutes in the NK1160-modified avidin solution in the above (8).

(10) The sensing chip was further washed with Tween 20 potassium thiocyanate, after which it was excited with a He-Ne laser system using the single-laser fluorometric system illustrated in FIG. 2. Fluorescence could be detected up to 3 ng/ml.

EXAMPLE 14

The plastic optical fiber with a 3-butenyl group introduced thereon obtained in Example 13 (3) was immersed in a 2 mg/ml aqueous osmium tetroxide solution at room temperature for 24 hours, after which the optical fiber was taken out from the solution and washed with distilled water. The optical fiber was then immersed in an ice-cooled 1M aqueous sodium metaperiodate solution for 2 hours under ice cooling conditions. The optical fiber was then washed with distilled water, etc. to yield a plastic optical fiber having formyl groups on a core surface thereof. Using this plastic optical fiber in the same manner as in Example 13 (4) through (10), the human pancreatic amylase antibody was measured. The antibody could be detected up to 4 ng/ml.

EXAMPLE 15

Formyl groups were introduced on a core surface of an optical fiber in the same manner as in Example 13 (1) through (3) except that 5-methyl-3-hexen-1-al was used in place of 4-penten-1-al in Example 13 (2). The optical fiber having formyl groups thus obtained was treated in the same manner as in Example 13 (4) through (10). The target substance could be detected up to 3 ng/ml.

EXAMPLE 16

(1) A plastic optical fiber made of polymethyl methacrylate (produced by Mitsubishi Rayon Co., Ltd.) was cut into a 3 cm piece. Both ends were polished with a polishing film, using ethanol as a lubricant.

(2) 10 mg of $NiSO_4$ was dissolved in 3 ml of water to yield an aqueous Ni solution. To 0.4 ml of a 20 mM KOH solution, 0.1 ml of the Ni aqueous solution and 50 $\mu$l of 3-hydroxypropanal were added to yield a treating solution.

(3) Next, a human pancreatic amylase antibody was assayed in the manner as in Example 13 (3) through (10). The target substance could be detected up to 3 ng/ml.

COMPARATIVE EXAMPLE 6

An optical fiber was treated in the same manner as in Example 13 except that glutaraldehyde was used in place of 50% 4-penten-1-al in Example 13 (2) and the optical fiber was not subject to oxidation treatment in the above (3). When the optical fiber thus obtained having on a core surface thereof a dialdehyde group bound thereto was used for immunoassay in the same manner as in Example 13, turbidity occurred on a core surface, and the target substance could be detected only up to 30 ng/ml, indicating a reduced assay sensitivity.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing a plastic optical fiber having formyl groups on a core surface thereof, comprising the step of immersing the core surface of a plastic optical fiber, selected from the group consisting of polystyrene, polyacrylic ester, polyester, polyacrylamide, polyvinyl alcohol, polyethylene terephthalate, polycarbonate and copolymers thereof, in a treating solution containing from 0.5 to 40 mM alkali metal hydroxide and a compound having formyl groups, in water or lower alcohol solvent to introduce formyl groups on the core surface.

2. The method according to claim 1, wherein the concentration of said compound having formyl groups in the treating solution is 0.2 to 1M.

3. The method according to claim 1, wherein said treating solution further contains Ni salt and wherein the concentration of said Ni salt is not higher than 0.9 mM.

4. The method according to claim 1, wherein said alkali metal hydroxide is at least one member selected from the group consisting of potassium hydroxide, sodium hydroxide and lithium hydroxide.

5. The method according to claim 1, wherein said lower alcohol is at least one member selected from the group consisting of methanol, ethanol, propanol and butanol.

6. The method according to claim 1, wherein said compound having formyl groups is a compound represented by Formula (2):

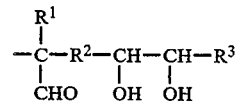
(2)

wherein $R^1$ represents a hydrogen atom, a lower alkyl group of $C_1$ to $C_3$ or a hydroxyl group; and $R^2$ represents —$(CH_2)_n$— and n represents an integer of 0 to 6.

7. A method for producing a plastic optical fiber having formyl groups on a core surface thereof, comprising the steps of reacting, at a temperature of 45°–60° C. for 5 to 20 minutes, the core surface of a plastic optical fiber, selected from the group consisting of polystyrene, polyacrylic ester, polyester, polyacrylamide, polyvinyl alcohol, polyethylene terephthalate, polycarbonate and copolymers thereof, with a compound represented by Formula (3):

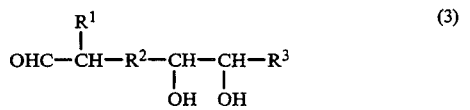
(3)

wherein $R^1$ represents a hydrogen atom, a lower alkyl group of $C_1$ to $C_3$ or a hydroxyl group; $R^2$ represents —$(CH_2)_n$— and n represents an integer of 0 to 6; and $R^3$ represents a hydrogen atom or an alkyl group of $C_1$ to $C_6$, to introduce on the core surface vic-diol groups represented by Formula (4):

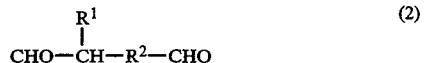

wherein $R^1$, $R^2$ and $R^3$ are the same as above, and then oxidizing the vic-diol groups to introduce formyl groups on the core surface.

8. A method for producing a plastic optical fiber having formyl groups on a core surface thereof, comprising the step of reacting, at a temperature of 45°–60° C. for 5 to 20 minutes, the core surface of a plastic optical fiber, selected from the group consisting of polystyrene, polyacrylic ester, polyester, polyacrylamide, polyvinyl alcohol, polyethylene terephthalate, polycarbonate and copolymers thereof, with a primary aldehyde alcohol to introduce primary hydroxy groups on the core surface, and then oxidizing the primary hydroxyl groups to introduce formyl groups on the core surface.

9. The method according to claim 8, wherein said primary aldehyde alcohol is a compound represented by Formula (5):

(5)

wherein $R^1$ represents a hydrogen atom, a lower alkyl group of $C_1$ to $C_3$ or a hydroxyl group; and $R^2$ represents —$(CH_2)_n$— and n represents an integer of 0 to 6.

10. The method according to claim 8, wherein the core surface of the plastic optical fiber is reacted with the primary aldehyde alcohol by a heat treatment in alkaline alcohol or water.

11. The method according to claim 8, wherein an oxidant used in oxidation of the primary hydroxyl groups bound to the core surface of the plastic optical fiber is pyridinium chlorochromate or pyridinium dichromate.

12. A method for producing a plastic optical fiber having formyl groups on a core surface thereof, comprising the steps of reacting, at a temperature of 45°–60° C. for 5 to 20 minutes, the core surface of a plastic optical fiber, selected from the group consisting of polystyrene, polyacrylic ester, polyester, polyacrylamide, polyvinyl alcohol, polyethylene terephthalate, polycarbonate and copolymers thereof, with a compound represented by Formula (6):

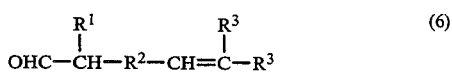
(6)

wherein $R^1$ represents a hydrogen atom, a lower alkyl group of $C_1$ to $C_3$ or a hydroxyl group; $R^2$ represents —$(CH_2)_n$— and n represents an integer of 0 to 6; and $R^3$ represents a hydrogen atom or an alkyl group of $C_1$ to $C_6$, to introduce on the core surface alkenyl groups represented by Formula (7):

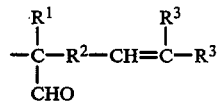

wherein $R^1$, $R^2$ and $R^3$ are the same as above, and then oxidizing the alkenyl groups to introduce formyl groups on the core surface.

13. The method according to claim 12, wherein the core surface of the plastic optical fiber is reacted with the compound represented by Formula (6) by a heat treatment in alkaline alcohol or water.

14. The method according to claim 12, wherein the oxidation of said alkenyl groups on the core surface is carried out by immersing said core surface in a lower alcohol or water, and then passing ozone-oxygen mixed gas stream to introduce formyl groups on the core surface.

15. The method according to claim 12, wherein the oxidation of said alkenyl groups on the core surface is carried out by treating with osmium tetroxide and then with metaperiodate.

16. A method for producing a plastic optical fiber having formyl groups on a core surface thereof, comprising the step of immersing the core surface of a plastic optical fiber, selected from the group consisting of polystyrene, polyacrylic ester, polyester, polyacrylamide, polyvinyl alcohol, polyethylene terephthalate, polycarbonate and copolymers thereof, in a treating solution containing from 0.5 to 40 mM alkali metal hydroxide and a compound having formyl groups, in water or lower alcohol solvent to introduce formyl groups on the core surface wherein said immersion step comprises a heat-treatment at a temperature of 45°–60° C. for 5 to 20 minutes.

* * * * *